United States Patent [19]

Mizukami et al.

[11] Patent Number: 4,746,608

[45] Date of Patent: May 24, 1988

[54] PROCESS FOR PRODUCING PEPTIDES

[75] Inventors: Tamio Mizukami, Machida; Seiga Ito, Sagamihara; Tetsuo Oka, Yokohama; Tatsunari Nishi, Tokyo, all of Japan

[73] Assignee: Kyowa Hakko Kogyo Co., Ltd., Tokyo, Japan

[21] Appl. No.: 732,828

[22] PCT Filed: Aug. 22, 1983

[86] PCT No.: PCT/JP83/00273

§ 371 Date: Apr. 12, 1985

§ 102(e) Date: Apr. 12, 1985

[87] PCT Pub. No.: WO85/01066

PCT Pub. Date: Mar. 14, 1985

[51] Int. Cl.[4] .................. C12P 21/00; C12P 21/02; C12P 21/04; C12N 15/00; C12N 1/20; C12N 1/00

[52] U.S. Cl. ........................... 435/68; 435/70; 435/71; 435/172.1; 435/172.3; 435/253; 435/320; 435/811; 935/33; 935/34; 935/38; 935/43; 935/61; 935/73

[58] Field of Search ............... 435/68, 70, 71, 91, 435/172.1, 172.3, 253, 317, 183–234, 317.1, 320; 935/33–48, 61

[56] References Cited

FOREIGN PATENT DOCUMENTS 0041313 12/1981 European Pat. Off. ......... 435/172.3
0083069  7/1983 European Pat. Off. ......... 435/172.3

OTHER PUBLICATIONS

Taniguchi et al, Proc. Natl. Acad. Sci. USA 77: 5230 (1980).
Hallewell et al, Gene 9: 27 (1980).
Herendeen et al, J. Bacteriol. 139(1), 185 (1979).
Patent Abstracts of Japan, vol. 7, No. 259, 58-141796, 8/23/83.

Primary Examiner—James Martinell
Attorney, Agent, or Firm—Fitzpatrick, Cella, Harper & Scinto

[57] ABSTRACT

A peptide can be produced in a high yield by culturing a microorganism containing a recombinant DNA comprising a eukaryotic gene coding for the peptide, a vector and a promoter which is capable of producing the peptide in a medium at a temperature 10° to 25° C. lower than the optimum growth temperature for the microorganism.

The invention is advantageously applicable to the production of peptides such as interferon.

12 Claims, No Drawings

PROCESS FOR PRODUCING PEPTIDES

TECHNICAL FIELD

The present invention relates to a process for producing physiologically active peptides derived from eukaryotes, for example, β-interferon (hereinafter referred to as β-IFN), by fermentation.

BACKGROUND ART

Recently, genes coding for useful, physiologically active peptides derived from eukaryotes, for example, β-IFN have been cloned and linked to promoters derived from microorganisms to efficiently produce the desired physiologically active peptides in microorganisms by utilizing rapidly developed genetic engineering techniques [T. Taniguchi, et al.: Proc. Jap. J. Acad. sec B 55, 464–469 (1979), Japanese Published Unexamined Patent Application No. 77654/82, Japanese Published Unexamined Patent Application No. 110600/83].

DISCLOSURE OF THE INVENTION

A technique of efficiently culturing microorganisms harboring recombinant plasmids according to their properties and producing desired physiologically active peptides in a high yield by fermentation is very important.

Generally, the optimum conditions for producing proteins and enzymes by microbial cells need not always be identical with the optimum growth conditions for the cells themselves, and greatly depend on culturing conditions such as culturing temperature, pH, and aeration-agitation and medium conditions. The production process also greatly depends on whether the desired protein or enzyme is of induction type or of constitution type. For example, in the case of induction type, the production amount greatly varies with the conditions for adding an inducer, etc. When the desired protein or enzyme is unstable, it is necessary to study the process for stable production.

The present inventors have studied various culturing conditions described above for producing the desired, physiologically active peptides in a high yield by fermentation, using microorganisms having recombinant plasmids and capable of producing β-IFN, etc. As a result, the present inventors have successfully found the conditions for highly efficient production of physiologically active peptides such as β-IFN, and have established the present invention.

The present invention is described in detail below.

The present invention provides a process for producing a peptide by culturing a microorganism containing a recombinant DNA comprising a gene coding for the peptide derived from eukaryotes, a vector and a promoter and being capable of producing the peptide in a medium, accumulating the peptide in the culture broth, and recovering the peptide from the culture broth, characterized by conducting the culturing at a temperature 10° to 25° C. lower than the optimum growth temperature for the microorganism.

Up to now, various physiologically active peptides have been expressed in microorganisms, and in most cases, Escherichia coli has been used as the microorganisms. In the case of Escherichia coli, the culturing is usually carried out at a temperature of 37° C., and actual production of these physiologically active peptides is mostly carried out at 37° C. In accordance with the present invention, peptides can be efficiently produced by culturing at a temperature 10° to 25° C. lower, preferably 15° to 20° C. lower than the ordinary culturing temperature. For example, in the case of Escherichia coli, a good result can be obtained by culturing at 15° to 30° C., preferably at 20° to 25° C.

In the present invention, peptides such as insulin, interferon, growth hormone, etc., preferably human β-interferon peptide, can be mentioned as the peptides derived from eukaryotes. As the vector, vectors derived from Escherichia coli, vectors derived from Bacillus subtilis, and vectors derived from yeasts, preferably pBR322, pBR313 and pMB9 derived from Escherichia coli, can be used. As the promoter, lac promoter, phoA promoter, trp promoter, etc., preferably trp promoter can be used.

As the medium for the present process, a medium usually used for culturing host microorganisms can be used. Generally, an enriched medium is preferred for improving the growth of microorganisms, but when trp promoter is used as the promoter, a peptone-based medium is not preferable.

When the production of peptides is controlled by trp promoter, it is known to add 3-indolylacrylic acid (IAA) as an inducer.

The present invention also provides a process for greatly improving the effect of the addition of IAA. Production of the peptides can be improved by adding IAA to the medium in the period from the latter half of the logarithmic growth phase to the maximum growth during the culturing of microorganisms, that is, in the case of using Escherichia coli, when the microorganisms grow to a range of 3 to 30 mg/ml in terms of dry cell concentration. IAA is added in a range of 10 to 200 mg/l. To further improve the production of peptides, IAA is further added continuously or intermittently after said addition of IAA. In the case of continuous addition, the total amount of IAA added should not be over the concentration of 200 mg/l, and in the case of intermittent addition, addition of 5 to 50 mg/l IAA should be made to 3 to 10 times.

The increase in peptide production by the above-described improvements in culturing process such as culturing at a low temperature, selection of time for adding IAA and supplementary addition of IAA has been known in neither of the process for producing peptides using ordinary microorganisms and that using the recombinant DNA techniques, and has been found by the present inventors for the first time.

BEST MODE FOR CARRYING OUT THE INVENTION

Examples of the present invention are given below.

Example 1

Productivity of human β-IFN is investigated by culturing Escherichia coli K-12 strain HB101 containing recombinant plasmid PLV-1 constructed by inserting a human β-IFN gene downstream from the trp promoter (hereinafter referred to as Ptrp), that is, Escherichia coli ILV-1 ATTCC 39023 (Japanese Published Unexamined Patent Application No. 110600/83) in the following manner.

Cells of the strain are cultured at 30° C. for 17 hours in LG medium prepared by dissolving 10 g of trypton, 5 g of yeast extract, 5 g of NaCl and 2 g of glucose in 1 l of water and adjusting the pH to 7.0 with NaOH. Then, 50 ml of the culture broth is inoculated in a 2

1-mini-jar fermenter containing 1 l of MGC medium (0.6% NaHPO$_4$, 0.3% KH$_2$PO$_4$, 0.5% NaCl, 0.1% NH$_4$Cl, 0.5% glucose, 0.5% casamino acid, 1 mM MgSO$_4$ and 4 mg/l thiamine) to conduct main culturing. To the culture broth is added ampicillin at a concentration of 50 mg/l. Culturing is carried out at various temperatures of 15° to 37° C. with aeration and stirring (1 vvm, 750 rpm), while controlling the pH to 6.5. Feeding is adjusted to a range of 0 to 1.0% while investigating with a glucose analyzer. Casamino acid is fed in the same amount as that of glucose.

When the cells grow to a dry cell concentration of 3 mg/ml, 20 mg/l IAA (made by Wako Junyaku Co.) is added thereto, and culturing is continued for 12 to 72 hours. Extraction of $\beta$-IFN from the cells is carried out in the following manner. One ml of the culture broth is centrifuged at 8,000 rpm for 10 minutes to collect the cells, and the cells are washed with 30 mM NaCl and then with 30 mM Tris-HCl (pH 7.5) buffer solution. The washed cells are suspended in said buffer solution, and admixed with 100 μg of lysozyme and 25 μl of 0.25M EDTA to make 1 ml of suspension. The suspension is left standing at 0° C. for 30 minutes, and the cells are disrupted by 3 repetitions of freezing and thawing. Then, the suspension is centrifuged at 15,000 rpm for 30 minutes to obtain a supernatant, and the amount of $\beta$-IFN in the supernatant is quantitatively determined according to the method of Armstrong [Armstrong, et al.: Appl. Microbiol., 21, 723–725 (1971)] wherein Vesicular Stomatitis Virus is used as the virus, and wherein cells derived from human amnion cells are used as the animal cells.

The results are shown in Table 1.

TABLE 1

| Temperature | Maximum $\beta$-IFN activity (units/l) |
|---|---|
| 15 | $1.1 \times 10^9$ |
| 20 | $3.8 \times 10^9$ |
| 25 | $2.5 \times 10^9$ |
| 30 | $4.7 \times 10^8$ |
| 37 | $1.1 \times 10^8$ |

As is obvious from Table 1, the productivity of $\beta$-IFN considerably depends on the culturing temperature, and very high productivity of $\beta$-IFN can be obtained by conducting the culturing at a temperature of about 20° C.

Example 2

Culturing is carried out under the same culturing conditions as in Example 1, except that strain ILV-1 is used, the culturing temperature is fixed at 20° C., and IAA is added at the time shown in Table 2, to investigate the time of adding IAA. The concentration of added IAA is 20 mg/l. The results are shown in Table 2.

TABLE 2

| Dry cell concentration when IAA is added (mg/ml) | Maximum $\beta$-IFN activity (units/l) |
|---|---|
| 1.0 | $1.3 \times 10^8$ |
| 2.1 | $9.4 \times 10^8$ |
| 3.0 | $1.9 \times 10^9$ |
| 4.0 | $3.2 \times 10^9$ |
| 7.5 | $2.5 \times 10^9$ |
| 15. | $1.9 \times 10^9$ |

As is obvious from Table 2, the productivity of $\beta$-IFN considerably depends on the cell concentration when IAA is added, and very high productivity of $\beta$-IFN can be obtained by the addition in the period from the latter half of logarithmic growth phase to the maximum growth.

Example 3

Productivity of $\beta$-IFN is investigated by carrying out culturing in the same manner as in Example 1, except that strain ILV-1 is used, the culturing temperature is 20° C., 20 mg/l IAA is added when the dry cell concentration reaches 3 mg/ml, and 5 successive additions of IAA are further made to one sample at every 12 hours with the concentration of 20 mg/l for each addition while no further addition is made to the other sample.

The results are shown in Table 3.

TABLE 3

| Time after the initial addition of IAA (hours) | $\beta$-IFN activity (units/l) | |
|---|---|---|
| | Without supplemental addition of IAA | With supplemental addition of IAA |
| 24 | $1.5 \times 10^9$ | $1.8 \times 10^9$ |
| 48 | $9.0 \times 10^8$ | $3.7 \times 10^9$ |
| 72 | $3.4 \times 10^8$ | $5.0 \times 10^9$ |

We claim:

1. A process for producing a human peptide which comprises the steps of culturing in a medium a microorganism which harbors a recombinant DNA comprising a gene coding for said peptide, a vector and a promoter, said microorganism being capable of producing the peptide, accumulating the peptide in the culture broth, and recovering the peptide from the culture broth, wherein the culturing step is conducted at a temperature 10° to 25° C. lower than the optimum growth temperature for the microorganism and within the range of 15° to 30° C.

2. A process according to claim 1, wherein the promoter is a tryptophan promoter.

3. A process according to claim 1 or 2, wherein a predetermined amount of 3-indolylacrylic acid is added to the medium in a period starting from the latter half of logarithmic growth phase and ending at the maximum growth during the culturing of the microorganism.

4. A process according to claim 3, wherein after the addition of said predetermined amount of 3-indolylacrylic acid, additional 3-indolylacrylic acid is added either continuously or intermittently.

5. A process according to claim 1, wherein the peptide is a human $\beta$-type interferon peptide.

6. A process according to claim 1, wherein the culturing is conducted at a temperature of 20° to 25° C.

7. A process according to claim 6, wherein the vector is selected from the group consisting of pBR322, pBR313 and pMB9.

8. A process according to claim 1, wherein the promoter is selected from the group consisting of lac, phoA and trp.

9. A process according to claim 3, wherein said predetermined amount of 3-indolylacrylic acid is from 10–200 mg/l.

10. A process according to claim 4, wherein the total concentration of 3-indolylacrylic acid added is not more than 200 mg/l when said additional 3-indolylacrylic acid is added continuously.

11. A process according to claim 4, wherein said additional 3-indolylacrylic acid is added intermittently in amounts of from 5–50 mg/l.

12. A process according to claim 11, wherein said additional 3-indolylacrylic acid is added intermittently from 3–10 times.

* * * * *